United States Patent [19]

Poile et al.

[11] Patent Number: 4,579,663

[45] Date of Patent: Apr. 1, 1986

[54] APPARATUS AND METHOD FOR OPTIMIZING SEPARATION OF AN UNKNOWN SAMPLE BY LIQUID CHROMATOGRAPHY

[75] Inventors: Anthony F. Poile, Ridgefield; Ralph D. Conlon, Wilton, both of Conn.

[73] Assignee: The Perkin-Elmer Corporation, Norwalk, Conn.

[21] Appl. No.: 653,256

[22] Filed: Sep. 24, 1984

[51] Int. Cl.$^4$ .............................................. B01D 15/08
[52] U.S. Cl. ................................... 210/656; 210/101; 210/198.2; 422/70; 436/161
[58] Field of Search ...................... 210/656, 659, 198.2, 210/96.1, 101; 422/70; 436/161

[56] References Cited

U.S. PATENT DOCUMENTS

| | | | |
|---|---|---|---|
| 3,997,298 | 12/1976 | McLefferty et al. | 210/198.2 |
| 4,066,879 | 1/1978 | Leaver | 210/198.2 |
| 4,364,263 | 12/1982 | Sankoorikal et al. | 210/198.2 |
| 4,455,084 | 6/1984 | Webb, Jr. | 210/659 |
| 4,468,331 | 8/1984 | Antle et al. | 210/198.2 |
| 4,478,713 | 10/1984 | Girot et al. | 210/198.2 |

OTHER PUBLICATIONS

Radio Shack Catalog No. RSC-9, Tandy Crop., Ft. Worth, Texas, p. 47, 1983.
Microcomputers in Chemical Engineering R&D, by Patterson, Chemical Engineering Progress, pp. 63–68, Nov. 1981.

Primary Examiner—John Adee
Attorney, Agent, or Firm—Francis L. Masselle; Edwin T. Grimes; Thomas P. Murphy

[57] ABSTRACT

An apparatus and method are disclosed to optimize resolution of unknown samples by liquid chromatography. A plurality of resolution experiments are performed where the solvents in the liquid chromatograph column are changed from one experiment to the next. The chromatogram for each experiment is analyzed to measure its peak resolution. A measure of peak resolution is displayed for each chromatograph thereby allowing the operator to select easily the chromatograms with the required peak resolution and determine the solvent conditions required to produce that resolution.

10 Claims, 6 Drawing Figures

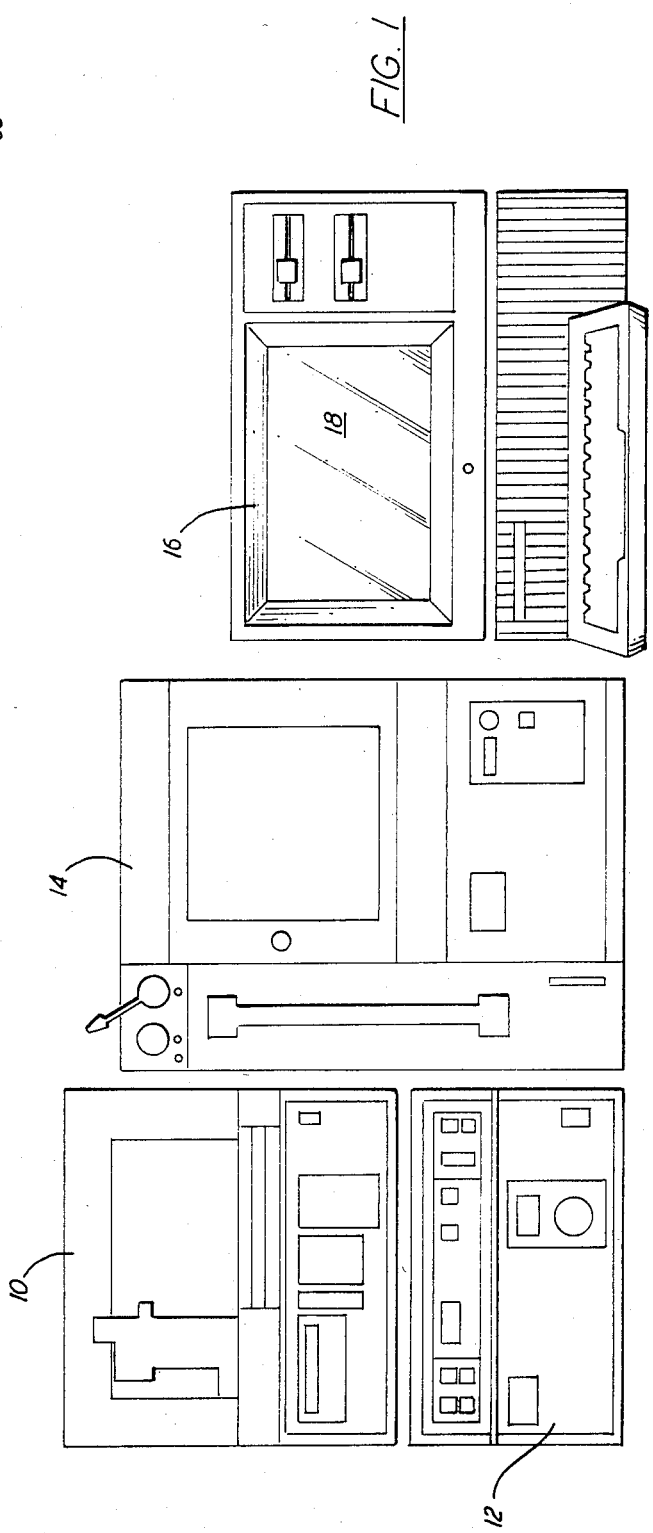
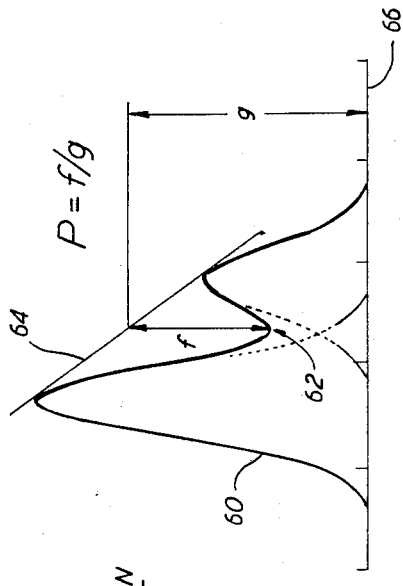
FIG. 5
PEAK RESOLUTION MEASUREMENT
FIG. 1

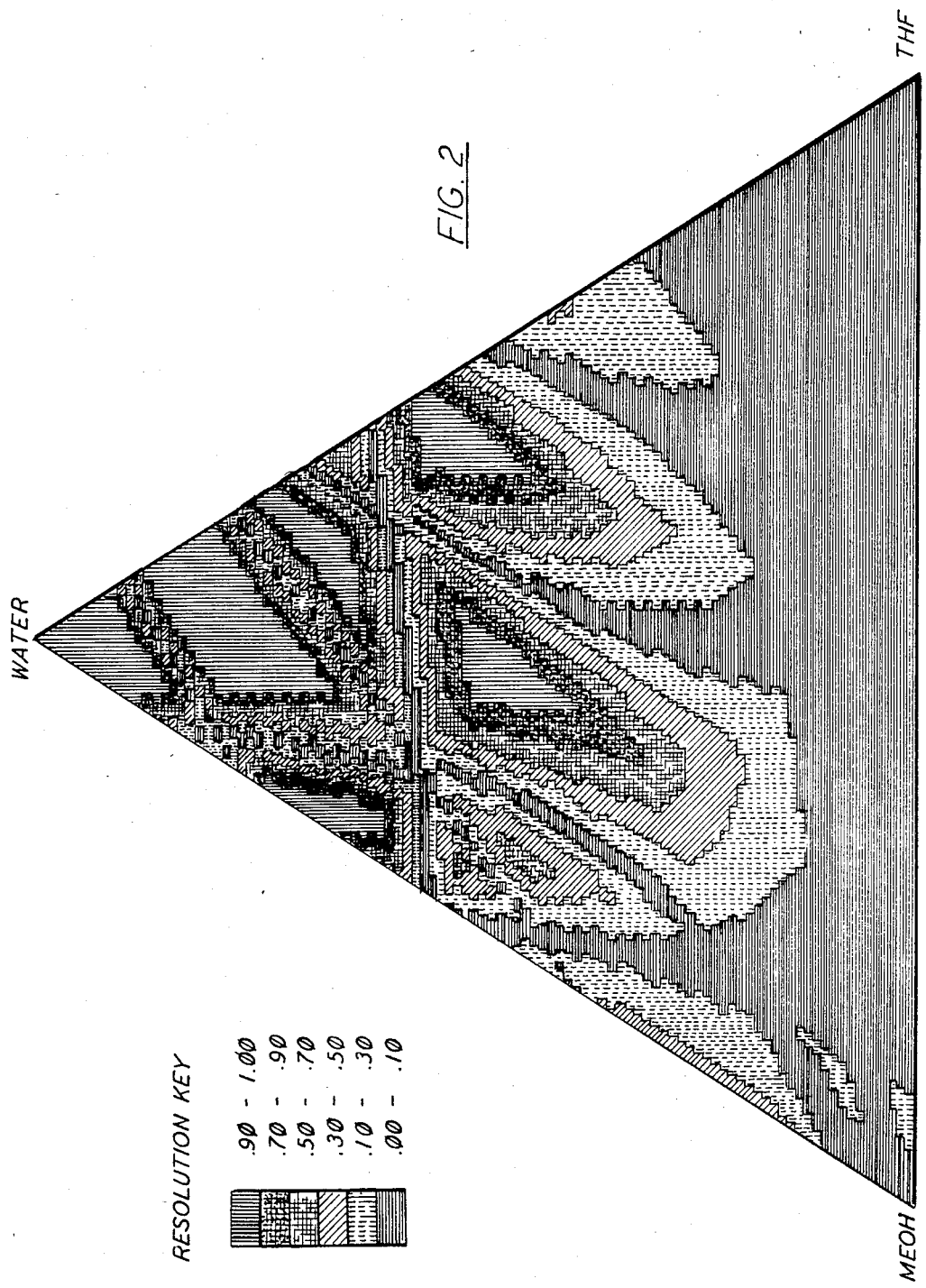

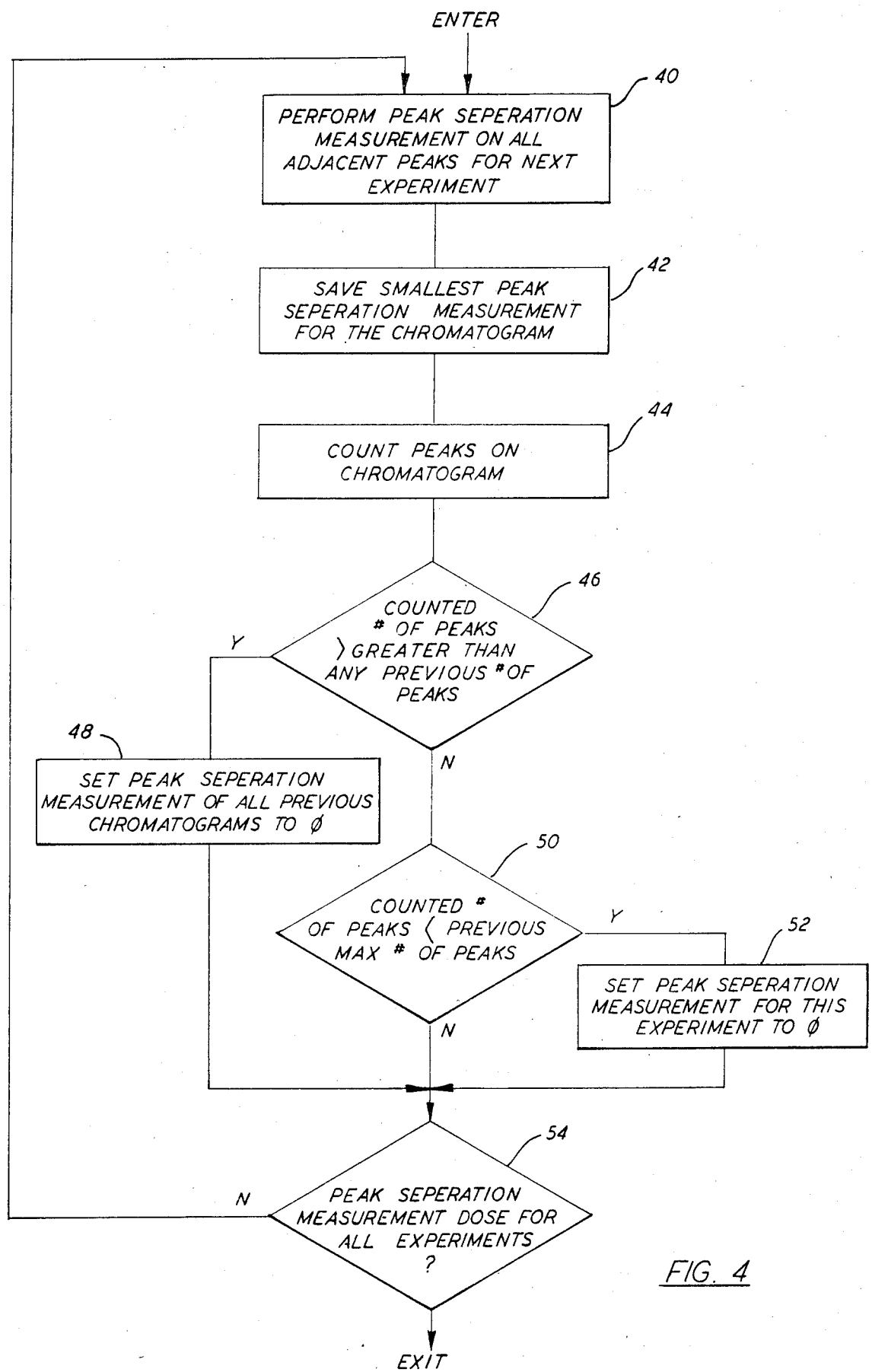

APPARATUS AND METHOD FOR OPTIMIZING SEPARATION OF AN UNKNOWN SAMPLE BY LIQUID CHROMATOGRAPHY

FIELD OF THE INVENTION

This invention relates broadly to the field of chromatographic analysis and particularly to a liquid chromatograph and a method for operating a liquid chromatograph so as to quickly choose from among many chromatograms those which are most meaningful for subsequent analysis.

BACKGROUND OF THE INVENTION

In the broad field of analytical instruments, chromatographs have been used to separate and measure the concentration of the constituents of complex mixtures. In liquid chromatography, an unknown sample is injected into a column having a liquid therein consisting of one or more liquid solvents. A detector at the base of the column detects the presence of the constitutents as they appear or elute from the bottom of the column. A plot of the detector output as a function of time, known as a chromatogram, is used by the chromatographer in his analysis of the unknown sample.

For example, it may be desired to know the concentration of a given medication in the blood stream of a patient. A known volume of blood would be entered into a chromatographic column and the constituent parts including the drug fraction would then separate out and be detected. The chromatogram would indicate the concentration of each component. By knowing when the medication should separate out, the therapeutic drug level of the medication can be determined. From that, the percentage of medication in the blood can be calculated.

The above described instrument and method of operation is very useful when the constituents of the sample are known. However, when the sample is an unknown, the chromatogram produced is more difficult to interpret. In addition, research has shown that the separation of unknowns into their constituent parts in a liquid chromatograph is not always possible with a given multi-solvent column solution. As a result, researchers must vary the concentration of the constituents of the column solution and have used column solutions having 3 or even 4 different constituents. This has improved the capability of the chromatographer to separate more kinds of unknowns into their component parts if a proper column solution can be selected. However, if an improper column solution is used, two or more components may co-elute thereby producing a chromatogram with insufficient resolution. Thus the chromatographer is left with the problem of randomly experimenting with the column solution constituents and evaluating the chromatogram for each such experiment to determine which one is best.

It is the last mentioned task which is very difficult. Typically, a chromatographer may perform a large number of experiments on a given unknown sample, each experiment being done with a different solvent mix in the column. The chromatograph produces a chromatogram from each experiment. For a typical unknown, the chromatographer may perform many experiments before he discovers a set of conditions which are acceptable if not ideal for his purposes. Some of the chromatograms are easily discarded as being unusable but evaluating the remaining chromatograms as to which is the most usable is very difficult. This task becomes more difficult as the number of experiments increases which is necessary when 3 or 4 solvents are used in the column. Without a system and protocol it becomes highly unlikely that an optimum separation will be achieved by trial and error.

It is therefore the primary objective of the present invention to provide a way to assist the chromatographer in selecting the liquid column solvents which will provide a chromatogram with good resolution for a given unknown sample injected into the column.

It is yet another objective of the present invention to provide a way to assist the chromatographer in selecting from a plurality of chromatograms the best chromatogram for use or further evaluation.

BRIEF DESCRIPTION OF THE INVENTION

The above-mentioned and other objectives of the invention are accomplished with a liquid chromatograph system of the present invention. The system includes an electrically controlled pump which controls the constituent mix for a plurality of liquid solvents used in the liquid chromatograph column. Sample injection means is provided to insert a known volume of sample solution into the column and a detector is used to detect the unknown sample constituents as they are separated out of the column. The detector creates a chromatogram which is stored for subsequent review. Thereafter, the column solvent mix is changed according to a predefined schedule of experiments and then the same unknown sample is automatically put into the column. A predetermined number of experiments are performed with different solvent mixes in the column and a sample of the unknown is put into the column at the start of each experiment.

Once each experiment is complete, the chromatogram for that experiment is analyzed. A rating is given to each chromatogram depending on the peak resolution thereof and if necessary, prior results are updated. When all the experiments are complete, the peak resolution ratings are plotted on a color graphical screen. The color at a given point tells the chromatographer the degree of resolution of the sample for the solvent proportions represented at that point in the display.

BRIEF DESCRIPTION OF THE DRAWINGS

The foregoing and other objects, advantages and features of the present invention are described further below in connection with the drawings which form a part of the disclosure wherein:

FIG. 1 illustrates the system components of the present invention.

FIG. 2 illustrates a typical color triangular display showing the results of many experiments using the apparatus of FIG. 1.

FIG. 3 and 4 are flow charts showing the manner in which the system elements of FIG. 1 operate in a timed sequence to perform a plurality of experiments and to produce a visual display of the results of each experiment.

FIG. 5 illustrates how the peak resolution measurement is performed.

DETAILED DESCRIPTION

Figure 2A:
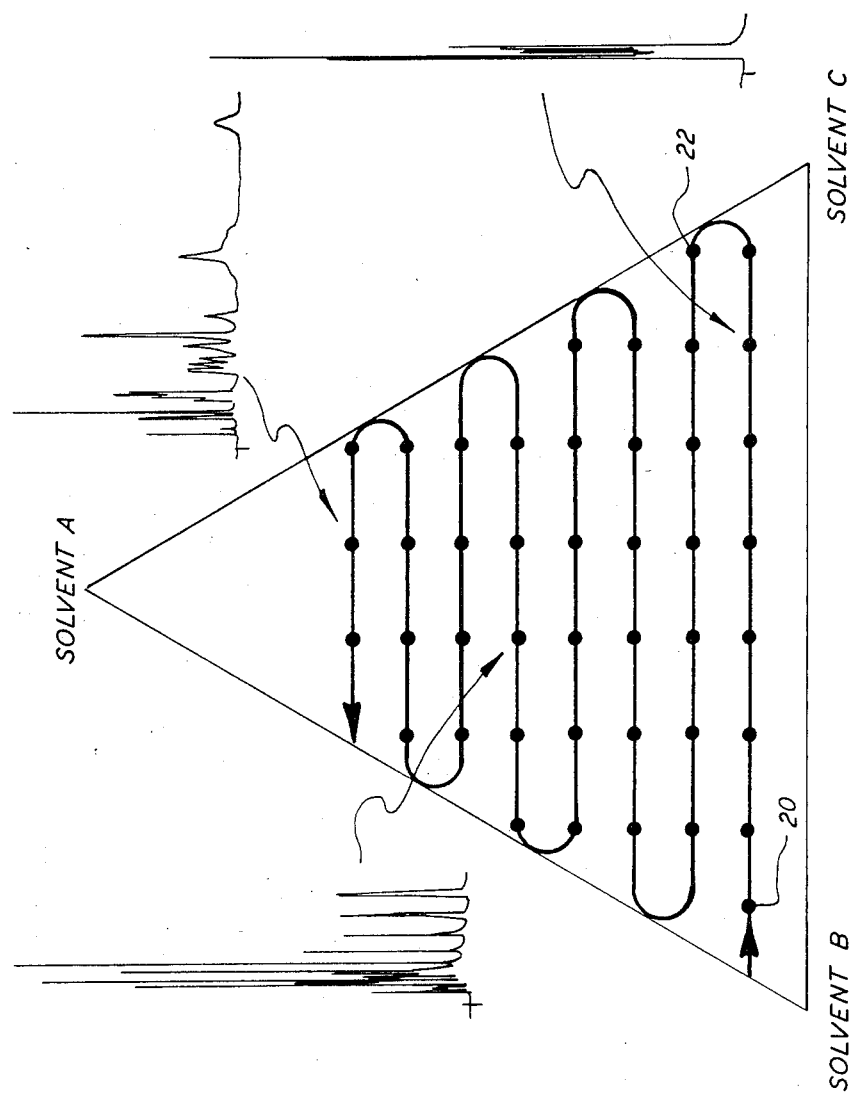
FIG. 2A illustrates how a plurality of experiments may be conducted to locate areas where other experiments should be conducted.

FIG. 1 illustrates the system components of the present invention. The system includes an auto sampler 10 which comprises a Perkin-Elmer ISS-100 or the like for removing samples from vials containing an unknown solution. This sampler is capable of taking samples from one of a plurality of sample vials and making the sample available for insertion into a chromatographic column. The column itself is located before the detector module 10 12 which in the preferred configuration comprises a Perkin-Elmer Model LC-95 or the like. For each experiment performed by this system, the auto sampler 10 provides a sample of the solution to be tested to the column and detector.

The system in addition includes a microprocessor controlled pump 14 which, in the preferred embodiment, comprises a Perkin-Elmer Series 4 pump assembly which includes a column oven. The microprocessor controlled pump 14 is operative to precisely control the solvent mix which is in the column used for separating the components of the sample introduced thereto.

The system of FIG. 1 additionally includes a computer module 16 which, in the preferred embodiment, comprises a Perkin-Elmer Model 7500 Professional Computer or the like. The computer module 16 is coupled by a data interface (not shown) to the auto sampler 10, the detector module 12, and the microprocessor control pump 14. In the preferred embodiment of the present invention, this interface comprises a Perkin-Elmer Model 316 data interface which merely serves as a communication adaptor between the computer module 16 and the detector located in the pump 14 assembly.

The computer module 16, by reason of the programs entered therein, is operative to supervise the activities of the auto sampler 10, the detector module 12, and the microprocessor control pump 14. Indeed, it is through the supervision provided by the computer module 16 that the operator is able to control the system elements to perform a desired set of experiments upon the unknown samples in the sample tray of the auto sampler 10. In addition, the screen 18 of the computer module 16 provides a means for displaying the results of experiments performed on the samples in the auto sampler 10. The screen 18 also serves as a means to display the system status.

FIG. 2 illustrates a typical triangular display showing the results of many experiments using the apparatus of FIG. 1. This display typically would appear on the screen 18 of the computer 16 and is readily usable by the chromatographer, in a manner later explained, to select the best chromatograms for the unknown sample which was tested by the apparatus of FIG. 1. The best chromatograms have a high degree of peak resolution and, therefore, these chromatograms are more useful to the chromatographer in determining the constituents of the sample being tested.

FIG. 2 also serves to illustrate the complexity of the problem faced by chromatographers today when using liquid chromatographs having column solutions with multiple components. In fact, it has been noted in the past by chromatographers that in such an experimental environment, there simply is no easy way to predict whether a given experiment will produce a chromatogram having meaningful results. Accordingly, chromatographers have in the past been forced to make a plurality of experiments on a given sample in order to subsequently evaluate the chromatograms produced thereby to determine which, if any, were useful to the chromatographer in determining the constituents of the sample. The difficulty of selecting the best chromatogram, as is easily understood, increases with the increase of the number of experiments performed on the sample. Indeed, the inventors themselves have had difficulty in deciding which chromatograms are useful in environments where as few as about 20 experiments have been performed. Where a larger number of experiments have been performed, this problem becomes more acute.

The apparatus according to the present invention, however, is operative to produce a display on the screen 18 such as illustrated in FIG. 2. This display is highly useful to chromatographers as it defines areas having chromatograms in which all components are completely resolved and, accordingly, these chromatograms are of the greatest use to the chromatographer. The display illustrated in FIG. 2 is capable of providing this aid to the chromatographer by reason of the fact that the shaded areas within the triangular shaped area on the screen are of different colors. The colors in turn are related to a quality value which is indicated in the key located to the left of the triangular area. In accordance with this key, those areas on the screen within the triangular area which are red have a peak resolution ranging between 0.9 and 1.0 although other ranges may be arbitrarily selected. Accordingly, chromatograms produced by experiments having solvent mixes occurring within the red areas provide the greatest resolution and, accordingly, are most useful to the chromatographer.

The pattern shown within the triangular shaped area of FIG. 2 was developed by the apparatus illustrated in FIG. 1 by performing a plurality of experiments on a given sample wherein the solvent in the column consisted of water, MEOH, and THF. The chromatogram produced for the sample for each solvent mix within the column was individually numerically analyzed to determine its resolution. Then, in accordance with the resolution key of FIG. 2, the area within the triangular shaped area of FIG. 2 corresponding to that particular solvent mix was colored in accordance with the resolution therefor as defined in the resolution key. Accordingly, the chromatographer can very easily select the chromatograms from amongst literally hundreds of chromatograms which will provide high resolution between the peaks of the chromatogram for the sample being tested. In the example selected, the chromatographer need only select chromatograms for experiments having solvent mixes in areas which are red within the triangular shaped area of FIG. 2.

Those of skill in the art will recognize that the triangular shaped area illustrated in FIG. 2 has been developed through the execution of many hundreds of experiments which, even though high speed liquid chromatography techniques are utilized, does take a great deal of time. In order to reduce the time necessary to locate solvent mixes which provide good resolution, a plurality of experiments may be conducted in a manner such as is illustrated in FIG. 2A. For example, an experiment might be conducted at a solvent mix illustrated at the dot 20 which might have, for example, a column solvent comprised of 10% of solvent A, 80% solvent B and 10% solvent C. After that, a plurality of experiments will be conducted wherein the percentage of solvent A remained at 10% while the percentage of solvents B and C are changed, for example, by approximately 10%.

Then a plurality of experiments would be conducted with the percentage of solvent A being raised to approximately 20%. One such experiment is represented at approximately point 22 wherein solvent A is approximately 20%, solvent B approximately 5% and solvent C approximately 75%. The experiments are continued until a sufficient number of experiments have been conducted so that dots representative of the experiment conditions substantially fill the triangular area of FIG. 2A. Thereafter, the chromatograms developed for each experiment are investigated to determine the peak resolution achieved thereby. Then, in accordance with techniques outlined later in this paper, the areas within the triangular area of FIG. 2A are illuminated with colors representative of the resolution achieved during the experiment conducted for the solvent mix represented at the center of the illuminated area. In this manner, the chromatographer can roughly determine areas within the triangular area of FIG. 2A which may yield good resolution for the chromatograms without conducting the hundreds of experiments necessary to provide the degree of resolution as illustrated in FIG. 2. Then, the chromatographer can instruct the apparatus of FIG. 1 to conduct a plurality of experiments in the isolated regions within the triangular area of FIG. 2A which appear promising, i.e, at locations near those having the best peak resolution. In this manner, the time required to produce chromatograms having good resolution is reduced from that required to produce the results illustrated in FIG. 2. Also, the reliability of obtaining meaningful results is greatly increased from that achieved by the hit and miss process of manual experiment selection.

It should also be noted that the apparatus of the present invention operates in a manner to minimize the equilibration (stabilization) time between experiments. As the chromatographer defines the maximum and minimum concentration of solvents and the amount of variation from one experiment to the next, the apparatus must then determine which experiment to perform first. It has been found that the equilibration time is minimized when the experiment sequence is established so that the experiment with strongest solvent mixtures are done first followed by experiments with progressively weaker solvent mixtures.

Figure 3:
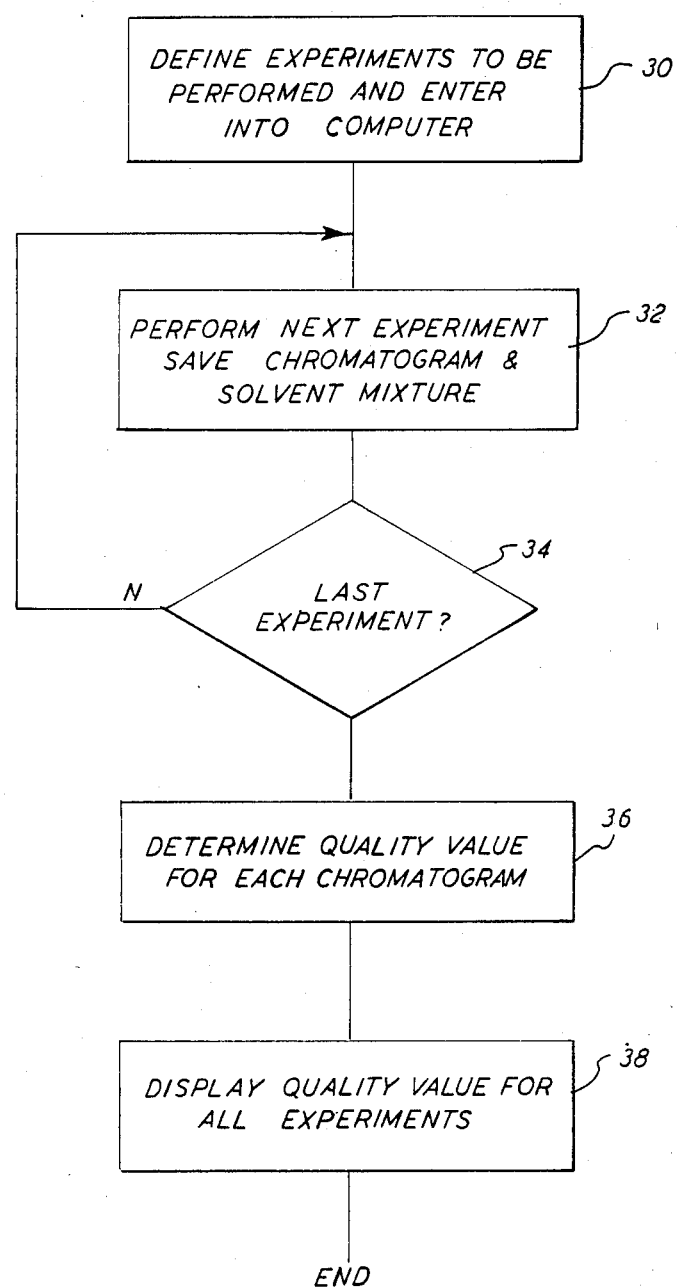

Referring now to FIG. 3, a flow chart is shown which illustrates the manner in which the apparatus in accordance with FIG. 1 operates in order to achieve the objectives of the present invention. As illustrated within box 30, the first step of the process according to the present invention is performed by the chromatographer who defines the boundaries and the step increment for a plurality of experiments to be conducted and the definition of these conditions is entered into the computer 16. Once the boundaries and step increment for the experiments have been defined, then the computer 16 takes over control of the apparatus illustrated in FIG. 1 and directs the microprocessor controlled pump 14 to equilibrate the column with the solvent mix desired for the first experiment. Then, the auto sampler 10 is instructed to withdraw a sample and insert it into the column and the detector 12 is instructed to detect the elution of the various components for the sample injected into the column. The output of the detector module 12 comprises a chromatogram which is then stored in the memory of the computer 16 along with the solvent mixture data for that chromatogram. This portion of the operation of the apparatus of FIG. 1 is illustrated by the description within the rectangular block 32 for the flow chart of FIG. 3.

Once one particular experiment is completed, the computer 16 inquires as to whether all experiments have been completed. This inquiry is illustrated by the diamond shaped box 34 of FIG. 3. In the event that the last experiment has not been performed, the computer 16 directs the auto sampler 10, the detector module 12 and the microprocessor control pump 14 to perform the next experiment in accordance with the new solvent mix as previously defined by the chromatographer.

This iterative looping of operations wherein an experiment is performed, a chromatogram is produced and saved and the solvent mix for that saved chromatogram is identified continues until all experiments have been performed. Then, as illustrated in the rectangular area 36, the computer determines a quality value for each experiment performed. The manner in which the quality value is determined is described in greater detail below in conjunction with FIG. 4. Once all the quality values have been determined for each stored chromatogram, the computer 16 then produces a display of the quality value associated with each experiment performed. In accordance with the present invention, where a column solvent is comprised of three different components, a triangular shape area of the type illustrated in FIG. 2 is produced. Those of skill in the art will recognize that the concepts of the present invention will apply equally to experiments with four solvents in the column. The display of experiment results with 4 solvents is a pyramid which cannot easily be displayed on the screen. In order to display the results of experiments involving four solvents, a plurality of triangular shaped areas of the type illustrated in FIG. 2 must be developed wherein each triangular shaped area has a fixed percentage of one solvent and the remainder of the solvents are determined in a manner well understood by liquid chromatographers from the triangular shaped area itself.

The manner in which the quality value for each chromatogram is determined is illustrated in the flow chart of FIG. 4. The flow chart illustrates in rectangular box 40 that the first step to be performed is to determine the peak separation measurement on all adjacent peaks for the chromatogram produced during an experiment. When the peak separation measurement is performed in accordance with the method described later in conjunction with FIG. 5, the peak separation measurement comprises a number ranging from 0 at a minimum to a maximum of 1.

Once the peak separation measurement has been performed on all adjacent peaks for a given experiment, the smallest peak separation measurement for that particular chromatogram is saved as is illustrated in rectangular box 42.

Once the peak separation measurement has been completed, then the number of peaks for that chromatogram is counted as illustrated in rectangular area 44. Once this is done, the results of the most recent peak counting operation is compared with those of all previous operations. In the event, as illustrated by the diamond shaped area 46, the number of counted peaks in the most recently analyzed chromatogram exceeds the number of peaks in any previously examined chromatogram, then the peak separation measurement for all previous chromatograms is set to 0 as illustrated in rectangular box 48 because at least 1 pair of peaks has 0 resolution. If the number of counted peaks in step 44 is less than the highest number of previous peaks for a given chromatogram, then the decision process illustrated in diamond shaped area 50 causes the peak separation measurement for the most recent experiment to be set to 0 as illustrated by the rectangular area 52. In the event that the decision illustrated by triangular block 50 results in a no answer, however, no change is necessary to the peak separation measurement and the process needs, thereafter, only determine whether all chromatograms have been investigated. This function is accomplished in the diamond shaped area 52. In the event that the processing of data for all experiments is not complete, the process returns to performing the peak separation measurement on all adjacent peaks for the next experiment as illustrated by rectangular box 40. The process described above continues until the peak separation measurement has been done for all experiments. When this occurs, the exit from the diamond shaped area 52 occurs and the remaining step is to display the quality values for all experiments as found in box 40 of FIG. 3.

As illustrated in FIG. 2, the quality values for given areas of the triangular area in FIG. 3 are established for experiments having peak separation measurements ranging for the values illustrated in the resolution key. The chromatographer need only know the color of the area giving the best resolution available to thereby select chromatograms which will be most useful for his investigation.

As mentioned earlier, the peak separation measurement utilized in accordance with the present invention has a value which ranges from 0 to a maximum of 1. The peak separation measurement is performed in a manner illustrated in FIG. 5. The chromatogram trace 60 for two adjacent peaks is analyzed in the computer 16 and the bottom of the valley between the two adjacent peaks 62 is located. Then a line 64 is drawn which connects the apices of the two peaks of the chromatogram trace 60 so that the line 64 is connected to portions of the trace 60 at each peak. Thereafter, the perpendicular distance f between the valley point 62 and the line 64 is determined. In addition, the distance between the intersection point of the perpendicular line f with the line 64 above the baseline 66 (g) is also determined. The peak separation measurement P is thereafter calculated by the formula $P = f/g$. Those of skill in the art will readily recognize that this method of determining peak separation measurement will produce numbers ranging between a value of 0 and 1. Those of skill in the art will recognize that any other peak separation measurement approach might also be utilized in conjunction with the present invention. Other peak separation measurement techniques, however, are not as useful if the number produced thereby does not range between 0 and 1 or any other finite range as it is more difficult with such a measurement scheme to determine which chromatogram amongst a plurality of chromatograms is best.

Those of skill in the art will recognize that the flow chart of FIG. 3 calls for the determination of quality values for each chromatogram after all the experiments have been performed. However, the quality value determination could be performed for each chromatogram at the conclusion of the experiment and prior to the beginning of the next experiment.

The foregoing description has made particular emphasis on the preferred embodiment. However, it will be clear to those skilled in the art that other equipment is suitable for modification to operate in the same manner. It is also clear that modifications can be made to the sequence of operations without departing from the spirit and scope of the invention as defined by the following claims.

What is claimed is:

1. A method for optimizing the separation of an unknown sample by liquid chromatography comprising the steps of:
    defining a plurality of liquid chromatograph experiments where each experiment is conducted with a different mixture of a plurality of solvents in a liquid chromatograph column;
    performing each said defined liquid chromatographic experiment and recording the chromatogram for each said defined experiment;
    determining the resolution of each said chromatogram where the maximum and minimum possible value of said resolution lies in a finite range; and
    displaying simultaneously a quality value for each said experiment where each quality value corresponds to a chromatogram having a resolution in a known subrange smaller than and included in said finite range.

2. The method of claim 1 wherein said quality value for any one experiment falls in the range between zero and one.

3. The method of claim 1 wherein said mixture of a plurality of solvents comprises at least three solvents.

4. The method of claim 1 wherein said displaying said quality values is done in a manner that the solvent mixture can easily be determined for each displayed quality value.

5. The method of claim 1 including the step of:
    counting the number of peaks in each chromatogram;
    setting each previously calculated resolution to zero for each chromatogram with fewer peaks than in the most recently calculated resolution; and
    setting the most recently calculated resolution to zero if fewer peaks are present than on any previously analyzed chromatogram.

6. The method of claim 4 including the step of:
    counting the number of peaks in each chromatogram;
    setting each previously calculated resolution to zero for each chromatogram with fewer peaks than in the most recently analyzed chromatogram; and
    setting the most recently calculated resolution to zero if fewer peaks are present than on any previously analyzed chromatogram.

7. The method of claim 1 wherein the experiments are performed in an order to minimize equilibration between experiments.

8. The method of claim 1 wherein the experiments are performed in a sequence where the solvent mixture used becomes progressively weaker from one experiment to the next.

9. A method for optimizing the separation of an unknown sample by liquid chromatography comprising the steps of:
    defining a plurality of liquid chromatography experiments where each experiment is conducted with a different mixture of a plurality of solvents in a liquid chromatograph column;
    performing each said defined liquid chromatography experiment and recording the chromatogram for each said defined experiment;
    measuring the length of a first perpendicular line between the valley between two adjacent peaks of each chromatogram and a second line drawn between the the apex of both adjacent peaks;

measuring the length of a second line drawn perpendicular to the base line between the intersection of said first line and said second line and the base line of the chromatogram;

forming a resolution value for the resolution of all adjacent peaks by forming the ratio of the length of said first line divided by the length of said second line and saving the smallest resolution value for all adjacent peaks for each chromatogram; and displaying simultaneously a quality value for each said experiment where each quality value corresponds to a chromatogram having a resolution value in a known finite range.

10. The method of claim 9 including the step of:

counting the number of peaks in each chromatogram;

setting each previously calculated resolution value to zero for each chromatogram with fewer peaks than in the most recently analyzed chromatogram; and setting the most recently calculated resolution value to zero if fewer peaks are present than on any previously analyzed chromatogram.

* * * * *